United States Patent
Williams et al.

(10) Patent No.: US 6,451,255 B1
(45) Date of Patent: Sep. 17, 2002

(54) DRY BOOSTER

(75) Inventors: Harold R. Williams, San Clemente, CA (US); Hans Strobel, Zurich (CH); Henry K. Hui, Laguna Niguel, CA (US); Leslie A. Feldman, Calabasas Hills, CA (US); Szu-Min Lin, Laguna Hills, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/472,319

(22) Filed: Dec. 23, 1999

Related U.S. Application Data

(63) Continuation-in-part of application No. 08/915,922, filed on Aug. 21, 1997, now Pat. No. 6,066,294.

(51) Int. Cl.⁷ .................................................. A61L 2/00
(52) U.S. Cl. ........................... 422/33; 422/28; 422/292; 422/295; 422/297; 422/300
(58) Field of Search .............................. 422/28, 33, 40, 422/292, 295, 297, 300

(56) References Cited

U.S. PATENT DOCUMENTS

| | | | |
|---|---|---|---|
| 4,410,492 A | 10/1983 | Kaye | 422/27 |
| 4,525,220 A | 6/1985 | Sasa et al. | 134/21 |
| 4,526,622 A | 7/1985 | Takamura et al. | 134/21 |
| 4,579,597 A | 4/1986 | Sasa et al. | 134/21 |
| 4,579,598 A | 4/1986 | Sasa et al. | 134/22.12 |
| 4,643,876 A | 2/1987 | Jacobs et al. | 422/23 |
| 4,756,882 A | 7/1988 | Jacobs et al. | 422/23 |
| 4,943,414 A | 7/1990 | Jacobs et al. | 422/28 |
| 4,956,145 A | 9/1990 | Cummings et al. | 422/28 |
| 5,084,239 A | 1/1992 | Moulton et al. | 422/22 |
| 5,186,893 A | 2/1993 | Moulton et al. | 422/23 |
| 5,244,629 A | 9/1993 | Caputo et al. | 422/22 |
| 5,288,460 A | 2/1994 | Caputo et al. | 422/23 |
| 5,310,524 A | 5/1994 | Campbell et al. | 422/33 |
| 5,413,758 A | 5/1995 | Caputo et al. | 422/22 |
| 5,580,530 A | 12/1996 | Kowatsch et al. | 422/102 |
| 5,733,503 A | 3/1998 | Kowatsch et al. | 422/28 |
| 6,083,458 A | 7/2000 | Lin et al. | 422/33 |
| 6,162,395 A * | 12/2000 | Kowanko | 422/28 |
| 6,312,646 B2 | 11/2001 | Kowanko | 422/33 |
| 6,365,103 B1 | 4/2002 | Fournier | 422/33 |

* cited by examiner

*Primary Examiner*—Robert J. Warden, Sr.
*Assistant Examiner*—Sean E. Conley
(74) *Attorney, Agent, or Firm*—Knobbe, Martens, Olson & Bear, LLP

(57) ABSTRACT

A method for sterilizing the interior of the lumen, where a dry booster which does not contain liquid and which has a volume at least 2 times the volume of the lumen is attached to the end of the lumen. The lumen and dry booster are placed in a sterilization chamber, and germicide is introduced into the chamber. A higher pressure is created outside the booster than inside the booster. The empty dry booster draws germicide into the lumen, sterilizing the interior of the lumen. The method can be enhanced by reducing the pressure in the chamber before introducing the germicide.

20 Claims, 1 Drawing Sheet

DRY BOOSTER

RELATED APPLICATIONS

This application is a continuation-in-part of application Ser. No. 08/915,922, filed Aug. 21, 1997, now U.S. Pat. No. 6,066,294.

BACKGROUND OF THE INVENTION

1. Field of the Invention

This invention relates to a method to sterilize articles such as medical instruments having long narrow lumens, and more particularly to a method for enhancing the effectiveness of the sterilization of the interior of the lumen.

2. Description of the Related Art

The need to sterilize articles such as medical instruments is well known. There are many methods of sterilization, including heat and chemical methods. Heat sterilization is normally done with steam. The heat or the moisture from the steam treatment damages many medical devices. As a result, chemical sterilization is commonly used.

Chemical sterilization uses a sterilizing fluid such as hydrogen peroxide, ethylene oxide, chlorine dioxide, formaldehyde, or peracetic acid. Although chemical sterilization is normally highly effective, chemical sterilization is less effective with medical devices containing long, narrow lumens, because it is difficult for the sterilizing agent to completely penetrate these long, narrow tubes. In order to enhance the penetration of the sterilizing agent though the entire length of the tube, several methods and several forms of apparatus have been developed to enhance the penetration of the sterilizing agent through long, narrow lumens.

For example, U.S. Pat. Nos. 4,410,492 and 4,337,223 describe an apparatus and a method for sterilizing lumens in which the lumen is placed in a socket connected to a circulating pump. The pump circulates the sterilizing gas through the lumen. Although the method is effective in sterilizing the lumen, the commercial apparatus uses ethylene oxide as a sterilant, and sterilization requires times of about 2–3 hours. Ethylene oxide is toxic. Additional aeration time is needed to remove the residual.

An apparatus and a method for delivering sterilizing agent directly into long, narrow lumens is described in U.S. Pat. Nos. 4,943,414, 5,580,530 and 5,733,503. The lumen is inserted into an adaptor connected to a small vessel containing hydrogen. peroxide. The adaptor and the vessel which contains the hydrogen peroxide are called the booster. The lumen, vessel, and adaptor are placed into a sterilization chamber. When the sterilization chamber is evacuated, the hydrogen peroxide vaporizes and passes through the lumen, providing the necessary hydrogen peroxide to the interior of the lumen. Although effective, the method has some disadvantages. First, in some forms of the apparatus, the booster must be "activated" manually by piercing a septum to make the hydrogen peroxide liquid accessible. Second, the booster is used only once before it is discarded. Third, the product has a limited shelf life. The storage and shipping conditions may affect the shelf life of the product.

There is a need for a method of sterilizing lumens which does not require the use of a booster with limited shelf life. Further, there is a need for a method which utilizes an apparatus which is reusable, to reduce costs.

SUMMARY OF THE INVENTION

One aspect of the invention involves a method for enhancing the sterilization of a lumen, where the lumen encloses an internal volume. The method includes attaching a dry booster to an end of the lumen, where the internal volume of the dry booster is at least 2 times the internal volume of said lumen and where the dry booster does not contain liquid. The method also includes placing the lumen and the dry booster in a chamber, introducing germicide into the chamber, and creating a higher pressure outside the dry booster than inside the dry booster. The method also includes flowing germicide from the chamber into the dry booster through the lumen, and sterilizing the lumen.

Advantageously, the dry booster includes an adaptor. Preferably, the dry booster includes a vessel. In some embodiments, the dry booster includes a flow restrictor. Advantageously, the dry booster includes a check valve. In an embodiment, the lumen is a plastic lumen. In another embodiment, the lumen is a metal lumen. Advantageously, the volume of the dry booster is at least 3 times the volume of the metal lumen.

The method may also include reducing the pressure in the chamber, evacuating the dry booster. Preferably, the pressure in the chamber is reduced below the vapor pressure of the germicide. Advantageously, the method also includes venting the chamber. Preferably, the method also includes generating a plasma in the chamber. In an embodiment, at least one step is repeated. Preferably, the germicide is a liquid, vapor, or gas. Advantageously, the germicide is hydrogen peroxide, ethylene oxide, peracetic acid, chlorine dioxide, or formaldehyde.

Another aspect of the invention involves a system for sterilizing a lumen, where the system includes a vacuum chamber, a pump to evacuate the chamber, a dry booster, where the dry booster is attachable to and detachable from the lumen, and where the internal volume of the dry booster is at least 2 times the volume of said lumen; and a source of germicide.

Preferably, the dry booster includes an adaptor. Advantageously, the dry booster includes a vessel. In an embodiment, the booster includes a flow restrictor. In another embodiment, the dry booster comprises a check valve.

DETAILED DESCRIPTION OF THE PREFERRED EMBODIMENTS

Figure 1:
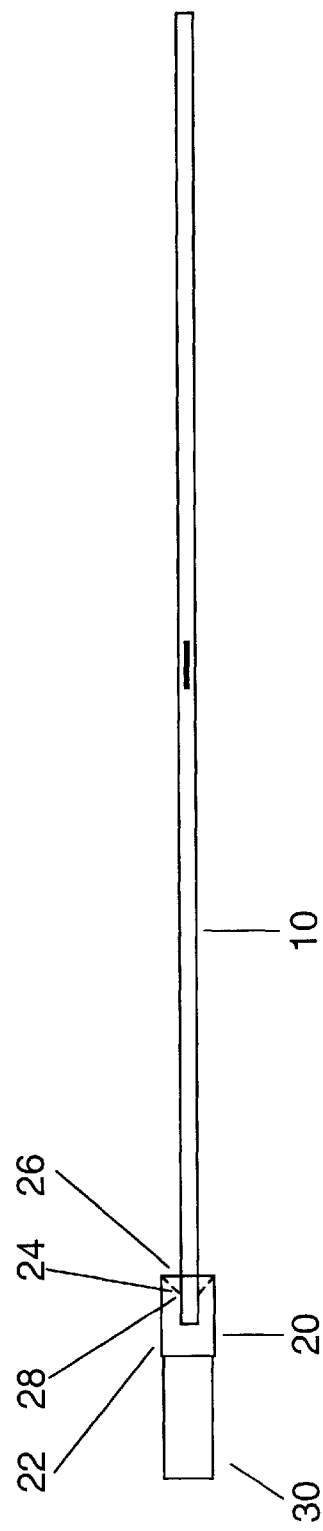
FIG. 1 is a schematic diagram of a lumen attached to an adaptor which is connected to a vessel according to an embodiment of the invention.

The method and device of the present invention relates to the sterilization of articles such as medical devices containing long, narrow lumens. The medical devices are devices such as endoscopes, catheters, tubing, or other instruments having lumens, where the device is preferably sterilized before use. Typical applications include surgery, medical applications, and the agricultural and fermentation industries.

The method has particular advantage in applications for sterilizing lumens having internal diameters of 3 mm or less or having a length of 27 cm or more, though the method is also applicable to lumens having wider diameters or shorter lengths. The germicides used with the method of the present invention are varied. Suitable germicides include glutaraldehyde, hydrogen peroxide, chlorine dioxide, or ethylene oxide. Unlike the other methods which use boosters, the germicide is not limited to being liquid at atmospheric pressure and a vapor at the temperature and pressure utilized in the sterilization process. Both vapor and liquid processes are applicable to the embodiments of the present method utilizing a dry booster. With the use of the device of the present invention, antimicrobial vapor is drawn through the lumen or interior of the tube of the instrument during the vapor sterilization process without the need to supply a separate vial of liquid germicide on the end of the lumen, as with the wet boosters previously used.

The procedure for vapor sterilization is generally as follows. The article to be sterilized is placed into the sterilization chamber, the chamber is sealed, and the chamber is evacuated to a pressure of less than about 50 torr, more preferably to 20 torr or less. An antimicrobial solution is then injected into the chamber, where it vaporizes and contacts the exposed surfaces of the article. The time necessary for total kill of specific microbial agents varies with the type and concentration of antimicrobials present and with the degree of exposure to the microbial agent. Microbials in cracks, crevices, mating surfaces, or diffusion restricted areas are somewhat protected from the antimicrobial agent and require more time for total kill than microbials on the external surface of the article. Heat or high frequency radiation such as plasma may be used to increase the effectiveness of the antimicrobial and its penetration into remote areas of the instrument.

The device of the present inventions comprises a vessel and a means for connecting the vessel directly to the lumen or the end of the tube of the article to be sterilized. Unlike the prior vessels, the vessel of the booster of the present invention does not contain antimicrobial solution. The booster devices in the past contained antimicrobial liquid which vaporized when exposed to vacuum. The antimicrobial vapor traveled from the vessel into the lumen.

In the present invention, the vessel attached to the lumen does not contain antimicrobial liquid. When the chamber is evacuated, the vessel, the lumen, and the means for connecting the vessel to the lumen are also evacuated. When antimicrobial vapor is injected into the chamber, the antimicrobial vapor is drawn into the lumen because of the vacuum from the large evacuated volume of the vessel attached to the lumen. Unlike the prior boosters, the antimicrobial vapor is drawn inward into the vessel from the sterilization chamber rather than being drawn out of the vessel into the sterilization chamber. Although in both cases, the antimicrobial vapor is drawn through the lumen, with the dry booster of the present invention, there is no need to have a vessel containing antimicrobial liquid.

A form of "dry booster" suitable for use in the method of the present invention is shown in FIG. 1. A lumen 10 is attached by a first end to an adaptor 20. The second end of the lumen is open to the interior of the sterilization chamber. The adaptor 20 shown in FIG. 1 is described in U.S. Pat. No. 5,580,530, herein incorporated by reference. The adaptor is shown as item 170 in FIG. 6 of U.S. Pat. No. 5,580.530. The adaptor 20 comprises a cylindrical tubular body 22 formed of a soft thermoplastic elastomer, such as Schafer, GmbH THEKA-FLEX, S 2030M or silicone. A truncated cone 24 extends inwardly, proximally, from a distal end 26 of the adaptor body and terminates in a central opening 28. The lumen 10 is inserted into the central opening 28 of the adaptor 20. The end of the adaptor 20 not having the truncated cone 24 is attached to a vial 30.

The vial 30 is a receptacle of any shape which encloses a substantial empty volume. Although the vial 30 of FIG. 1 is a cylinder, other shapes are suitable, including round, rectangular, square, elliptical, or any other suitable shape. All that is important is that the vial 30 and the adaptor 20 enclose a substantial volume of space which can be evacuated when the vial 30 is attached to the adaptor 20 and the lumen 10.

Other forms of adaptor 20 and vial 30 are suitable for use with the method of the invention. All that is necessary is that the adaptor 20 provide a fluid link between the lumen 10 and the vial 30 and that the vial 30 and adaptor 20 enclose sufficient volume relative to the volume of the lumen 10 to be sterilized. As will be shown below, the required ratio of the volume of the vial 30 and adaptor 20 relative to the volume of the lumen 10 depend on the process conditions in the sterilization. Some suitable forms of adaptor 20 and vial 30 for use in the method of the present invention are shown, for example, in FIGS. 1, 2, 2A, 3, and 3A of U.S. Pat. No. 5,580,530. The embodiments of the adaptor shown in U.S. Pat. No. 5,580,530 include an expandable sheath, a bushing comprising a series of rings of inwardly extending plastic flaps, a bushing with an aperture for attaching disposable cartridges, a drawstring on a pouch, and a "zip-lock" closure on a pouch. These forms of the adaptor 20 are illustrative only, and the method of the invention is not limited to these forms of adaptor 20.

The vial 30 can comprise any three dimensional container preferably of semi-rigid or rigid material, having an opening therein. The vial 30 may be made of, e.g., polyethylene, polypropylene, glass, or any other material which is compatible with the antimicrobial vapor. In the embodiments shown in FIGS. 3 and 3A of U.S. Patent No. 5,580,530, the vial 30 comprises a pouch. In the embodiments shown in FIGS. 1 and 2A of U.S. Pat. No. 5,580,530, the vial 30 comprises a vial. Any shape of vial 30 may be used in the method of the present invention. The major restriction on the vial 30 is that the vial 30 and adaptor 20 together have a volume larger than the volume of the lumen 10. The required ratio of the volume of the vial 30 and adaptor 20 relative to the lumen 10 depend on the process conditions, and the required ratios will be described in the Examples below.

Experiments were performed to compare the sterilization efficiency with and without a dry booster. In both sets of experiments, a biological indicator of $1.6 \times 10^6$ Bacillus stearothermophilus spores on a stainless steel wire was placed in the center of a stainless steel lumen 10. For the experiments in Example 1, both ends of the lumen 10 were left open. For the experiments with the dry booster in Example 2, the apparatus shown in FIG. 1 was used. A first end of the lumen 10 was attached to a first end of the adaptor 20 described in FIG. 6 of U.S. Pat. No. 5,580,530. The second end of the adaptor 20 was attached to an empty polyethylene scintillation vial 30 with 17 mm outside diameter. Vials 30 having varying lengths were tested to provide a range of volumes of adaptor 20 and vial 30 relative to the volume of the lumen 10. The sterilization results for the lumen without the dry booster are given in Example 1. The sterilization results for the experiments when the dry booster was attached to the lumen are given in Example 2.

EXAMPLE 1

Sterilization Results with No Dry Booster on the Lumen

In Example 1, biological indicators of $1.6 \times 10^6$ Stearothermophilus spores were placed in the center of lumens of various lengths. The lumens were placed in a 72.5-liter STERRAD 50 sterilizer with a standard STERRAD 50 load double wrapped with CSR wraps. The chamber was evacuated to 0.4 torr, and 740 mg of 59 weight % hydrogen peroxide were injected for 5 minutes to provide 6 mg/L of hydrogen peroxide vapor in the chamber. After 5 minutes of injection and diffusion, the chamber was vented to atmospheric pressure, the lumens were removed, and the sterility results of the biological indicators were determined. The results are shown in Table 1 below.

TABLE 1

Sterility Results From Tests with No Dry Booster
(No. of Positives/No. of Samples)

| Lumen Size | Sterility Results |
| --- | --- |
| 1 mm × 250 mm | 0/3 |
| 1 mm × 300 mm | 0/3 |
| 1 mm × 350 mm | 0/3 |
| 1 mm × 400 mm | 1/2 |
| 1 mm × 450 mm | 3/3 |
| 1 mm × 500 mm | 2/2 |

As shown by the results in Table 1 above, under the test conditions, the interiors of the 1 mm ID lumens longer than 350 mm were not sterilized by exposure to hydrogen peroxide vapor.

In Example 2, a "dry booster" comprising an adaptor 20 and a vial 30 containing no liquid sterilant was attached to one end of the lumen 10. All of the other test conditions were the same as in Example 1. The results in Example 2 demonstrate the improvement in sterilization efficiency of the interiors of long lumens when the "dry booster" according to an embodiment of the method of the present invention was attached to the end of the lumen 10 to be sterilized.

EXAMPLE 2

Sterilization of Lumens With A "Dry Booster"

In the experiments of Example 2, one end of an adaptor 20 as described in U.S. Pat. No. 5,580,530 was attached to an end of a 1 mm×400 mm stainless steel lumen to be sterilized. A biological indicator as described in Example 1 was placed in the center of each lumen. The second end of the adaptor 20 was attached to a 17 mm ID polyethylene scintillation vial 30 having varying lengths and therefore varying volumes, as shown in FIG. 1. The lumens 10 with the attached boosters comprising an adaptor 20 and vial 30 were exposed to hydrogen peroxide vapor under the conditions described in Example 1, the chamber was vented, and the sterility tests were measured. The results are shown in Table 2 below.

TABLE 2

Sterility Results From Tests with a Dry Booster
(No. of Positives/No. of Samples)

| Ratio of Dry Booster Volume/Internal Volume of 1 mm × 400 mm Lumen | Sterility Results |
| --- | --- |
| 20:1 | 0/3 |
| 15:1 | 0/3 |
| 14:1 | 0/3 |
| 13:1 | 0/3 |
| 12:1 | 0/3 |
| 11:1 | 1/3 |
| 10:1 | 1/3 |
| 5:1 | 1/2 |

A 1 mm×400 mm stainless steel lumen was chosen for the tests in Example 2, because the 400 mm lumen was the shortest lumen which was not sterilized without the need for a dry booster in Example 1.

There are two conclusions which can be drawn from the results shown in Table 2. First, use of a "dry booster" can enhance the sterilization of the interior of lumens. The interior of the 1×400 mm lumen in Example 1 was not sterilized. By contrast, the interior of the 1×400 mm lumen was sterilized in the majority of the examples shown in Example 2, where a dry booster was attached to the end of the 1×400 mm lumen.

Second, the interior of the 1×400 mm lumen was not sterilized unless the ratio of the dry booster volume (the volume of the adaptor 20 and the vial 30) was at least 12 times as large as the internal volume of the 1 mm×400 mm stainless steel lumen. In cases where the ratio of the volume was less than 12:1, not all of the samples were sterilized. A volume of dry booster to the volume of the lumen of 12:1 or more is therefore required for the dry booster to be effective in enhancing the sterilization of the interior of the lumen, under the conditions of Example 2.

The comparative results from Examples 1 and 2 demonstrate the improvement in sterilization efficiency for long lumens when a dry booster having a volume of 12 or more times the volume of the lumen is attached to the end of the lumen to be sterilized and the chamber was evacuated to a pressure of 0.4 torr before the hydrogen peroxide was injected into the chamber.

A series of experiments were performed to determine the sterilization efficiency at various initial vacuum pressures. The length of time for which the vacuum was maintained before injection of the hydrogen peroxide was also varied. The effects of pressure and length of the evacuation time are shown in Example 3 below.

EXAMPLE 3

Effects of Varying Evacuation Pressure and Evacuation Time

A plurality of 1 mm×500 mm stainless steel lumens 10, each containing a biological indicator, were placed in a 72.5 liter sterilization chamber as in Example 1. Dry boosters having various volumes were attached to the ends of certain of the lumens, as shown in FIG. 1. The remainder of the lumens were placed into the chamber without a dry booster. The chamber was evacuated to a pressure of either 0.4 torr or 0.1 torr and was maintained at the pressure of 0.4 torr or 0.1 torr for a time period of between 0 and 20 minutes, as noted in Table 3 below. A total of 740 mg of 59 weight % hydrogen peroxide was injected for 5 minutes to provide 6 mg/L of hydrogen peroxide vapor in the chamber. After 5 minutes of injection and diffusion, the chamber was vented to atmospheric pressure, the lumens were removed, and the sterility results of the biological indicators were determined. The results are shown in Table 3 below.

TABLE 3

Dependence of Sterility Results on Evacuation Pressure, Evacuation Time, Presence of a Dry Booster, and Volume Ratio of Dry Booster to Lumen
(No. of Positives/No. of Samples)

| Evacuation Conditions | | Sterility Results | | | |
| --- | --- | --- | --- | --- | --- |
| | | | Volume Ratio of Dry Booster to Lumen | | |
| Evacuation Pressure | Evacuation Time | No Booster | 10:1 | 5:1 | 3:1 |
| 0.4 torr | 0 minutes | 2/2 | 1/2 | 2/2 | — |
| 0.4 torr | 5 minutes | 2/2 | 0/2 | 2/2 | — |
| 0.1 torr | 0 minutes | 2/2 | 0/2 | 2/2 | — |

TABLE 3-continued

Dependence of Sterility Results on Evacuation Pressure, Evacuation Time, Presence of a Dry Booster, and Volume Ratio of Dry Booster to Lumen (No. of Positives/No. of Samples)

| Evacuation Conditions | | Sterility Results | | | |
|---|---|---|---|---|---|
| | | | Volume Ratio of Dry Booster to Lumen | | |
| Evacuation Pressure | Evacuation Time | No Booster | 10:1 | 5:1 | 3:1 |
| 0.1 torr | 10 minutes | 2/2 | 0/2 | 1/2 | 2/2 |
| 0.1 torr | 20 minutes | 1/2 | — | 0/2 | 0/2 |

There are several conclusions that can be drawn from the data in Table 3. First, the sterilization efficiency of the lumen improves with lower evacuation pressures and longer evacuation times. For example, sterilization with a 10:1 booster was not effective at 0.4 torr with no vacuum hold time. The sterilization was effective when the vacuum was maintained at a pressure of 0.4 torr for 5 minutes, however. Similarly, sterilization with a 10:1 booster was not effective with a sterilization pressure of 0.4 torr with no hold time, but the sterilization was effective at a pressure of 0.1 torr with no hold time.

Second, the sterilization efficiency with a dry booster was at least as high as with no dry booster in all cases.

Third, the sterilization efficiency improved with higher ratios of dry booster volume: lumen volume. All but 1 of the coupons were sterilized when a dry booster with 10 times the volume of the lumen was used. The sterilization efficiency steadily decreased as the ratio of the dry booster volume to the volume of the lumen decreased from a ratio of 10:1 to 5:1 and even further when the ratio decreased to 3:1.

Fourth, the ratio of the volume of the dry booster to volume of the lumen required to sterilize the interior of the lumen can be decreased by using lower evacuation pressures and longer evacuation times. In Example 2, ratios of dry booster volume/lumen volume of 12:1 were required to sterilize the interior of the lumens with evacuation pressures of 0.4 torr with no hold on the evacuation time.

In Example 3, the interior of the lumens could be sterilized when the volume of the dry booster (adaptor and vial):volume of lumen was 5:1 or even 3:1 when the pressure was reduced to 0.1 torr and the chamber was evacuated to 0.1 torr for 20 minutes. Evacuating the chamber to lower pressures for longer times therefore allows dry boosters with lower volumes relative to the volume of the lumen to be effective in sterilizing the lumens.

It is believed that the reason that the sterilization efficiency improves with longer evacuation times is because the increased exposure time to the vacuum removes more moisture from the lumen. When less moisture is present, more hydrogen peroxide can be drawn into the dry booster through the lumen.

In Example 4 below, a 1 mm×2000 mm TEFLON™ lumen was used rather than the 1 mm×500 mm stainless steel lumen of Example 3. The dependence of sterilization efficiency with evacuation pressure and evacuation time was studied.

EXAMPLE 4

Dependence of Sterility Results on Evacuation Pressure, Evacuation Time, Presence of a Dry Booster, and Volume Ratio of Dry Booster to Lumen With a TEFLON™ Lumen (No. of Positives/No. of Samples)

| Evacuation Conditions | | Sterility Results | | | |
|---|---|---|---|---|---|
| | | | Volume Ratio of Dry Booster to Lumen | | |
| Evacuation Pressure | Evacuation Time | No Booster | 3:1 | 2:1 | 1:1 |
| 0.4 torr | 0 minutes | 3/3 | 0/3 | 1/3 | — |
| 0.1 torr | 20 minutes | 1/2 | 0/2 | 0/2 | 2/2 |

Even with a dry booster volume:lumen volume of 3:1, all of the biological indicators in the 1 mm×2000 mm TEFLON™ lumens were sterilized with evacuation pressures of 0.4 and 0.1 torr. By contrast, when a 1 mm×500 mm stainless steel lumen was sterilized in Example 3, not all of the biological indicators were sterilized even with dry booster having a volume 5 times larger than the lumen. The stainless steel lumen was shorter than the TEFLON™ lumen, and the dry booster in the stainless steel lumen experiments had a higher volume relative to the volume of the lumen. Both the shorter length of the stainless steel lumen and the larger volume of the dry booster in the experiments in Example 2 should have improved the sterilization efficiency. Instead, the sterilization efficiency with the longer TEFLON™ lumen and the smaller dry booster of Example 4 was higher than with the stainless steel lumen in Example 3.

Further, when the chamber was evacuated to 0.1 torr for 20 minutes, sterilization of the TEFLON™ lumen was effective even when the ratio of the volume of the dry booster (adaptor 20 and vial 30) relative to the lumen 10 was as low as 2:1.

It is believed that the improved sterilization efficiency with the TEFLON™ lumen in Example 4 is due to the TEFLON™ lumen being less reactive with the hydrogen peroxide vapor. The comparative results of Examples 3 and 4 demonstrate that TEFLON™ lumens are easier to sterilize than stainless steel lumens.

The results of Examples 1–4 demonstrate that use of the "dry booster" can enhance the sterilization of the interior of lumens. Further, the ratio of the volume of the "dry booster" relative to the volume of the lumen required for sterilization of the interior of the lumen varies depending on the process conditions and the type of lumen to be sterilized. A volume ratio of 12:1 was required with evacuation pressures of 0.4 torr with no hold time with a stainless steel lumen, as shown in Example 2. When the pressure was reduced to 0.1 torr and the evacuation time was increased to 20 minutes, a volume ratio of 3:1 was required, as shown in Example 3. Sterilization of a TEFLON™ lumen at 0.1 torr and 20 minutes evacuation time was effective with a dry booster volume-:lumen volume of 2:1, as shown in Example 4. The sterilization efficiency with a "dry booster" therefore depends on both the process conditions and the type of lumen to be sterilized. Plasma may optionally be introduced to enhance the sterilization.

Figure 2:
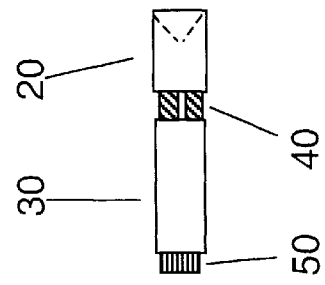
FIG. 2 is a schematic diagram of a lumen attached to an adaptor which is connected to a flow restrictor and a vessel according to an embodiment of the invention, where the vessel has a check valve.

FIG. 2 shows an alternative form of the "dry booster" with some enhancements over the "dry booster" of FIG. 1. The "dry booster" of FIG. 2 comprises an adaptor 20 and a vial 30 as does the "dry booster" of FIG. 1. The "dry booster" shown in FIG. 2 additionally comprises a flow restrictor 40 between the adaptor 20 and the vial 30. The flow restrictor 40 limits the flow of the antimicrobial vapor through the lumen 10, helping to maintain the pressure difference between the vial 30 and the lumen 10.

Further, the "dry booster" shown in FIG. 2 further comprises a check valve 50 on the vial 30. The check valve 50 allows the gas inside the vial 30 to be released from the vial 40 directly into the sterilization chamber rather than having to be evacuated through the lumen 10. The check valve 50 therefore reduces the length of time required to evacuate the vial 30.

The embodiments of the dry booster and the methods of sterilizing devices with the embodiments of the dry booster provide enhanced methods of sterilizing the interior of lumens without the need to attach boosters containing antimicrobial solutions.

The enhanced sterilization efficiency with the dry booster is probably due to the internal volume of the dry booster and the initial pressure difference between the inside and outside of the dry booster. The volume and the pressure act as a driving force to cause the flow of germicide into the booster through the lumen. The dry booster can also be applied to a liquid phase process or a process at a pressure higher than atmospheric pressure by creating a higher pressure outside the booster than inside the booster. The amount of germicide flow into the booster can be controlled by the volume of the booster. The liquid, gas, or vapor process can be enhanced by reducing the pressure in the booster and the lumen before introducing the germicide.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. A method for enhancing the sterilization of a lumen, said lumen enclosing an internal volume, said method comprising:
    attaching a dry booster to a first end of said lumen, said dry booster enclosing an internal volume, wherein the internal volume of said dry booster is larger than the internal volume of said lumen and wherein said dry booster does not contain liquid;
    placing said lumen and said dry booster in a chamber, wherein said chamber is at a pressure;
    introducing germicide into said chamber;
    creating a higher pressure outside the dry booster than inside the dry booster;
    flowing germicide from said chamber into said dry booster through said lumen; and
    sterilizing said lumen.

2. The method of claim 1, wherein said dry booster comprises an adaptor.

3. The method of claim 1, wherein said dry booster comprises a vessel.

4. The method of claim 1, wherein said dry booster comprises a flow restrictor.

5. The method of claim 1, wherein said dry booster comprises a check valve.

6. The method of claim 1, wherein said lumen is a plastic lumen.

7. The method of claim 1, wherein said lumen is a metal lumen.

8. The method of claim 1, wherein the internal volume of said dry booster is at least 2 times the volume of said lumen.

9. The method of claim 1, wherein the method further comprises reducing the pressure in said chamber, thereby evacuating said dry booster.

10. The method of claim 9, wherein the pressure in said chamber is reduced below the vapor pressure of the germicide.

11. The method of claim 9, wherein the method further comprises venting said chamber.

12. The method of claim 9, wherein the method further comprises generating a plasma in said chamber.

13. The method of claim 1, wherein at least one step is repeated.

14. The method of claim 1, wherein said germicide is a liquid, vapor, or gas.

15. The method of claim 1, wherein said germicide comprises hydrogen peroxide, ethylene oxide, peracetic acid, chlorine dioxide, or formaldehyde.

16. A system for sterilizing a lumen, said lumen enclosing an internal volume, said system comprising:
    a vacuum chamber;
    a pump to evacuate the chamber;
    a dry booster, wherein said dry booster is attachable to and detachable from the lumen, and wherein said dry booster encloses an internal volume, wherein the internal volume of the dry booster is at least 2 times the volume of said lumen; and
    a source of germicide.

17. The system of claim 16, wherein said dry booster comprises an adaptor.

18. The system of claim 16, wherein said dry booster comprises a vessel.

19. The system of claim 16, wherein said dry booster comprises a flow restrictor.

20. The system of claim 16, wherein said dry booster comprises a check valve.

* * * * *